US012539393B2

(12) United States Patent
Gilliland et al.

(10) Patent No.: US 12,539,393 B2
(45) Date of Patent: Feb. 3, 2026

(54) CATHETER

(71) Applicant: TRACELESS BIOPSY, LLC, Atlanta, GA (US)

(72) Inventors: Charles Gilliland, Atlanta, GA (US); Baylee Brooke Heard, Macon, GA (US); Ann Marie Stringer, Cheverly, MD (US); Asia Pauline Hernandez, San Diego, CA (US); Elizabeth Kaleigh Johnston, Suwanee, GA (US)

(73) Assignee: TRACELESS BIOPSY, LLC, Atlanta, GA (US)

( * ) Notice: Subject to any disclaimer, the term of this patent is extended or adjusted under 35 U.S.C. 154(b) by 0 days.

(21) Appl. No.: 18/595,839

(22) Filed: Mar. 5, 2024

(65) Prior Publication Data

US 2024/0198049 A1 Jun. 20, 2024

Related U.S. Application Data

(63) Continuation of application No. 16/393,113, filed on Apr. 24, 2019, now Pat. No. 11,938,280.

(Continued)

(51) Int. Cl.

| | |
|---|---|
| ***A61M 25/00*** | (2006.01) |
| ***A61M 25/04*** | (2006.01) |
| ***A61M 39/10*** | (2006.01) |

(52) U.S. Cl.

CPC ...... *A61M 25/0097* (2013.01); *A61M 25/007* (2013.01); *A61M 25/008* (2013.01);

(Continued)

(58) Field of Classification Search

CPC .... A61J 1/201; A61J 1/2096; A61M 25/0097; A61M 25/007; A61M 25/008; A61M 25/04; A61M 39/10; A61M 25/0017

See application file for complete search history.

(56) References Cited

U.S. PATENT DOCUMENTS 6,248,100 B1 * 6/2001 de Toledo ............. A61M 25/01 604/514

6,508,789 B1 * 1/2003 Sinnott ................. A61M 25/04 604/95.04

(Continued)

FOREIGN PATENT DOCUMENTS

KR 2019118046 A 10/2019

KR 20190118046 A * 10/2019 ........ A61M 25/0013

*Primary Examiner* — Rebecca E Eisenberg

*Assistant Examiner* — Kate Elizabeth Strachan

(74) *Attorney, Agent, or Firm* — Perilla Knox & Hildebrandt LLP

(57) ABSTRACT

A drainage catheter system comprising a catheter having an elongate body \configured for insertion into an organ or cavity of a patient and a hub configured for coupling with a longitudinal shearing device and the first end of the catheter and movable over the elongate body of the catheter. A locking stay suture extends through the elongate body of the catheter. The length of the elongate body of the catheter can be adjusted by sliding the hub coupled to the longitudinal shearing device along the longitudinal axis of the catheter, and then creating a longitudinal cut in the catheter through which the proximal end of the locking stay suture can be removed and secured, thereby enabling the excess catheter tubing to be removed by cutting and allowing the base to rest flush against the patient's body.

8 Claims, 8 Drawing Sheets

Related U.S. Application Data

(60) Provisional application No. 62/661,760, filed on Apr. 24, 2018.

(52) U.S. Cl.
CPC ............ *A61M 25/04* (2013.01); *A61M 39/10* (2013.01); *A61M 25/0017* (2013.01); *A61M 2039/1083* (2013.01)

(56) References Cited

U.S. PATENT DOCUMENTS

| | | | | |
|---|---|---|---|---|
| 2007/0032779 | A1* | 2/2007 | Accisano .......... | A61M 25/0097 604/541 |
| 2007/0049905 | A1* | 3/2007 | Magnusson ........... | A61M 25/04 604/540 |
| 2014/0276655 | A1 | 9/2014 | Murray et al. | |
| 2017/0224967 | A1* | 8/2017 | Gorn ................... | A61M 25/007 |
| 2017/0232231 | A1* | 8/2017 | Neoh ................ | A61M 25/0133 604/539 |
| 2018/0071493 | A1* | 3/2018 | Konstantarakis .. | A61B 17/0487 |

* cited by examiner

CATHETER

CROSS-REFERENCE TO RELATED APPLICATIONS

This application is a continuation of U.S. patent application Ser. No. 16/393,113 filed Apr. 24, 2019, which claims the benefit of U.S. Provisional Patent Application Ser. No. 62/661,760 filed Apr. 24, 2018, the entireties of which applications are hereby incorporated herein by reference for all purposes.

TECHNICAL FIELD

The present invention relates generally to the field of, and more particularly to, the field of catheters and of securing drainage catheters in the body for long-term use, and more particularly to systems, apparatus, and methods for customization of catheter length to increase patient comfort and reduce or eliminate complications resulting from fitting patients with catheters that are too long for their individual needs and/or that project a distance away from the body at the insertion site.

BACKGROUND

Drainage catheters may be placed in patient organs for periods of time ranging from days to weeks during which the patients may be released from the hospital. These patients may wish to run errands, attend medical appointments, or even return to work prior to catheter removal. Although several lengths of drainage catheter exist, patient body size and anatomy can differ, and depth of placement can also differ depending on the desired insertion site. When a catheter with the exact length required for the patient is not available, a longer one must be used. Typical hubs with ports for connecting to drainage bags are fixed in place at the ends of drainage catheters. Longer catheters may protrude from the patient's body by from one to several inches and the tubing and hubs are prone to becoming stuck on furniture, clothing, or bedding. This can cause discomfort or, at the worst, may pull on the catheter, dislodging it and causing pain as well as increasing infection risk. Protruding catheters may limit patient mobility since drainage bags and connecting tubing at a distance from the body may be difficult to conceal under clothing. Ideally, catheter length could be adjusted for individual patient circumstances and to ensure the catheter hub sits flush with the patient's skin, but currently-existing catheters cannot be cut without also severing the locking stay sutures that keep their ends in position inside the patient's body.

Furthermore, the hard material of many catheters and hubs can press into the wearer's skin, causing pain and ulcers. A catheter made of a flexible material and a hub that can be covered with a softer material would prevent these problems.

The present invention is directed primarily to the provision of a length-adjustable catheter which can be cut by a novel cutting mechanism without severing the internal locking stay suture, a separate removable hub, and a soft silicone cover meeting these and other needs. The hub can use existing standard connections such as, for example, a luer lock connector, for attachment to tubing or another drainage device. This relative ease of use allows for the catheter and hub/port to be maintained at home by the patient to some degree instead of in a medical setting. Further, the shape of the connector or adapter can allow for tubing to run down the vertical surface of the body rather than extending outwardly from the body.

SUMMARY

In example embodiments, the present invention provides a universal drainage catheter kit and system and method of adjusting the same to account for different insertion depths, patient body conditions, and the like. In example forms, the catheter kit includes a catheter having an elongate body, a separate hub configured to surround the elongate body of the catheter, and a longitudinal shearing device configured to attach to the hub.

In one aspect, the present invention relates to a catheter having an elongate body extending a length along a longitudinal axis from a proximal first end to a distal second end, the second end configured for insertion into an organ or cavity of a patient. The catheter further has an end hole at the distal second end as well as a plurality of distal side holes. When the catheter is placed in a patient, drainage of fluids from a cavity or organ in the patient is accomplished by fluid flow into the end and/or side holes, through the body of the catheter, and out through the hub to tubing, a drainage bag, pump, syringe, or other collection device. In some aspects, the collection device can be removed and the hub can be capped if drainage is not required for the moment but catheter removal is not yet indicated. The elongate body of the catheter is constructed from a sturdy, flexible material that can be sheared with a blade but is not typically torn or damaged under conditions of regular use. The elongate body surrounds a locking stay suture extending from an attachment point at the end hole of the distal second end, through one of the side holes, through the elongate body of the catheter along the longitudinal axis, and out through the proximal first end of the catheter. In one aspect, the flexible material of the hub contributes to increased patient comfort.

In another aspect, the invention relates to a hub and longitudinal shearing device configured to attach to the catheter. In example forms, the hub and longitudinal shearing device are manufactured separately from the catheter and are placed on the catheter at the time of insertion and adjustment. The hub is molded of plastic or a similar stiff material and includes a first surface and a second surface. The first surface of the hub is configured to attach to the longitudinal shearing device and further incorporates a female luer lock connector for attachment to tubing, a cap, or a collection device as described previously. The second surface of the hub includes a silicone ring configured to surround the elongate body of the catheter. A channel extends from the opening of the silicone ring, through the body of the hub, allowing for the hub to advance along the placed catheter towards a body surface of the patient. The hub optionally includes a locking arm that can be flipped down to secure the locking stay suture, or another feature to secure the locking stay suture, for example by winding, tying, clamping, and so forth. The longitudinal shearing device contains a blade capable of producing a longitudinal cut along the longitudinal axis of the catheter without damaging the locking stay suture inside the catheter. In example forms, the longitudinal shearing device includes two portions that can be removed from the hub separately once shearing has been completed.

In still another aspect, the invention relates to a method for inserting a catheter into a patient, securing the catheter in the patient, and adjusting the catheter length so that the catheter hub rests against the patient's body with no parts of the catheter extending past the hub or projecting outwardly from the body surface. In one example system and method, a catheter having an elongate body extending along a longitudinal axis and containing an internal locking stay suture is inserted through a body surface into an organ, cavity, or other area of interest by placing the end hole over a sharp needle stylet that has been previously directed into the area by an interventional radiologist. A metal stiffening cannula may also be used as an alternative to the sharp needle stylet to guide catheter placement. The catheter hub attached to the longitudinal shearing device is placed at the proximal end of the catheter, away from the patient's body surface and with the silicone ring facing the body surface.

In example forms, the, catheter hub and longitudinal shearing device are advanced along the catheter until the silicone ring on the hub is flush with a patient's body surface, creating a longitudinal cut along the axis of the catheter. The longitudinal shearing device is then removed from the catheter hub. The proximal end of the locking stay suture is then slipped through the longitudinal cut in the catheter and tightened by pulling or another mechanism, forming a pigtail structure or curl in the distal end of the catheter by pulling the end hole toward one of the plurality of side holes, securing the catheter in the organ or area of interest. The suture is then secured by any of several mechanisms such as, for example, by depressing a locking side arm on the catheter hub to hold the suture in place, or by tying, winding, or clamping, thereby maintaining the pigtail structure to prevent the catheter from pulling or slipping out of the insertion site.

Once the locking stay suture is secured, preferably the excess catheter containing the longitudinal slit can be cut using shears or another bladed device. A zip tie, suture clamp, or other means can then be used to tighten the silicone ring of the hub around the catheter. In example forms, a soft silicone cover is placed over the hub at the body surface. The cover can be tapered, contoured, or padded to increase patient comfort and prevent the catheter from being pulled out and can have adhesive on one side to adhere the cover to the skin. A luer lock connector on the hub can then be used as an attachment point for tubing, a syringe, a pump, a collection bag, or a cap, as needed.

In one aspect, the drainage catheter is capable of sustaining a drainage flow rate of at least 2.4±0.3 mL/s of fluid with no external applied forces (i.e., no pumping). In example forms, the pigtail curled structure can withstand greater than 2 pounds of pulling force without becoming uncurled and without the catheter becoming dislodged from the body or the placement site within the body.

In other aspects, the system and method described herein contain numerous features designed to enhance patient comfort. The elongate body of the catheter is flexible rather than rigid, which prevents pain or discomfort from motion. The external port (luer lock connector) of the catheter is flush with the base of the catheter, and the base rests against the patient's skin, so no portion of catheter extends away from the body unsupported. Although the base is made from a stiff material, it is surrounded by a silicone cover that can possess optional features (tapering, contouring, and/or padding) to prevent pressure from the hub against the skin. The silicone cover can further be attached to the patient's skin with adhesive to prevent friction or rubbing injuries. If a portable drainage bag is required, it can be secured against the patient's body, under clothing, presenting an unobtrusive profile and allowing for the patient to dress normally.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

BRIEF DESCRIPTION OF THE DRAWINGS

In FIG. 4A, the locking stay suture has not yet been tightened. In FIG. 4B, the suture is pulled to achieve tightening. In FIG. 4C, the locking side arm is flipped down to secure the suture in place.

In FIG. 8A, a catheter containing an internal locking stay suture is inserted into an organ or area of interest over a wire that has been previously directed into the organ. In FIG. 8B, the wire is removed from the catheter. In FIG. 8C, a catheter hub and longitudinal shearing blade are advanced along the catheter until the silicone ring on the hub is flush with a patient's skin, creating a longitudinal cut along the axis of the catheter. In FIG. 8D, the end of the locking stay suture is slipped through the longitudinal cut in the catheter. In FIG. 8E, the suture is tightened, forming a pigtail structure or curl in the end of the catheter, securing the catheter in the organ or area of interest; the suture is then secured by any of several mechanisms. In FIG. 8F, the longitudinal shearing device is removed from the catheter. In FIG. 8G, the catheter can be cut at the base of a female luer lock connector on the catheter hub and the hub is tightened around the catheter at the silicone ring by any of several means including the use of a zip tie. In FIG. 8H, a soft silicone cover can be placed over the hub at the skin; the cover may be tapered, contoured, or padded to increase comfort and prevent the catheter from being pulled out and may have adhesive on one side to adhere the cover to the skin. In FIG. 8I, a drainage bag is affixed to the female luer lock connector on the catheter hub.

DETAILED DESCRIPTION OF EXAMPLE EMBODIMENTS

The present invention may be understood more readily by reference to the following detailed description of example embodiments taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
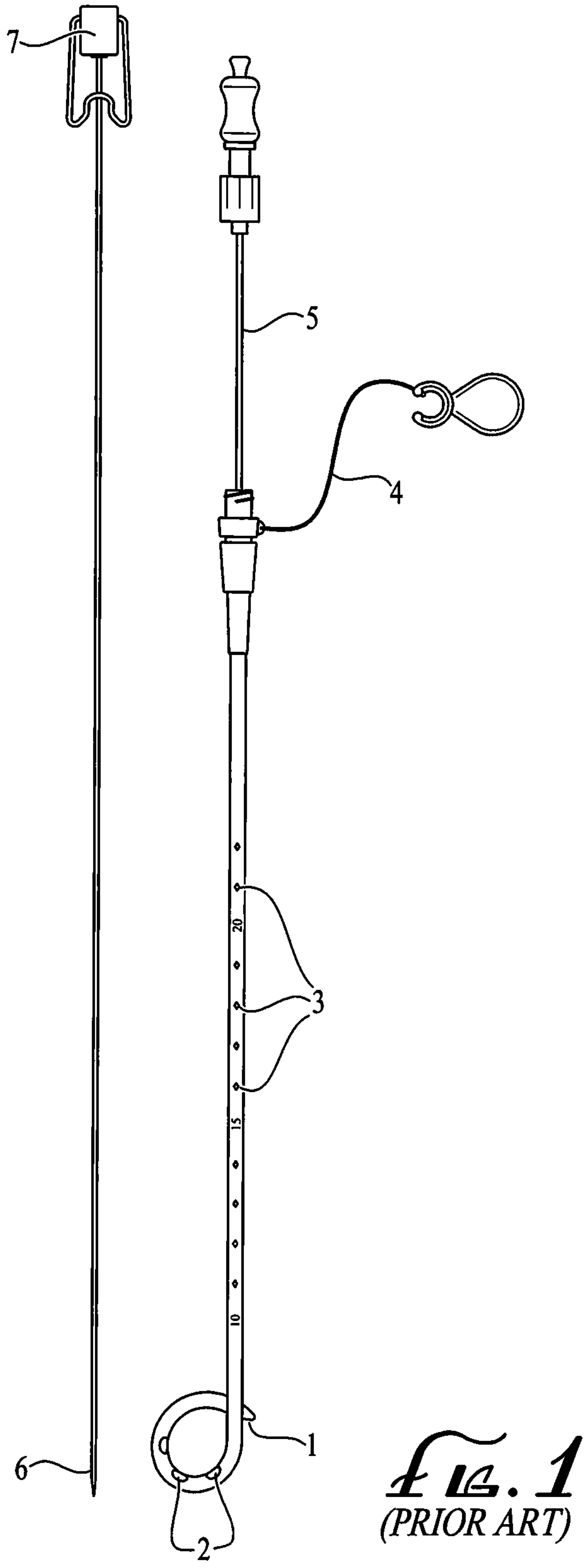
FIG. 1 (PRIOR ART)
FIG. 1 shows a side view of an example prior art catheter.

With reference now to the drawing figures, wherein like reference numbers represent corresponding parts throughout the several views, FIG. 1 shows a side view of an example prior art catheter. The catheter has an elongated body composed of a flexible material having end hole 1 and a plurality of side holes 2 which are used for drainage of fluids from the point of insertion into the catheter. The elongated body of the catheter can optionally have hash marks 3 indicating various lengths. A locking stay suture 4 connects through the end hole 1 to one of the side holes 2 and extends through the length of the elongated body of the catheter. Catheter placement typically is accomplished by an interventional radiologist and may optionally include a first step of placement of a sharp needle stylet 6 in the patient's body using an imaging method such as, for example, X-ray imaging or ultrasound, in conjunction with any required contrast agents for visualization purposes. Optionally, a metal stiffening cannula 5 can be used to guide the elongated catheter body over the sharp needle stylet 6. End hole 1 of the catheter can be placed over the sharp needle stylet 6 and the elongated body of the catheter can be guided over the sharp needle stylet 6, stopping when the desired depth of placement is achieved. When used, metal stiffening cannula 5 provides a degree of stiffness to the flexible catheter body for catheter placement purposes.

Figure 2:
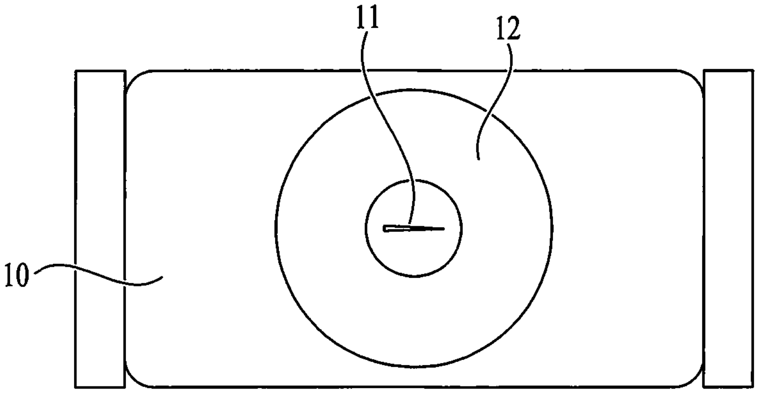
FIG. 2 is a top view of an assembled catheter hub locked to a longitudinal shearing device according to one embodiment of the present invention.

FIG. 2 is a top (plan) view of an assembled catheter hub locked to a longitudinal shearing blade according to one embodiment of the present invention. Catheter hub 10 connects to silicone ring 12 and silicone ring 12 is designed and configured to grip and connect to the elongated body of the catheter. Catheter hub 10 connects to a shearing device (not seen in this view) that includes longitudinal shearing blade 11, which can be used to cut the catheter along its length without damaging the locking stay suture that extends the length of the catheter.

Figure 3:
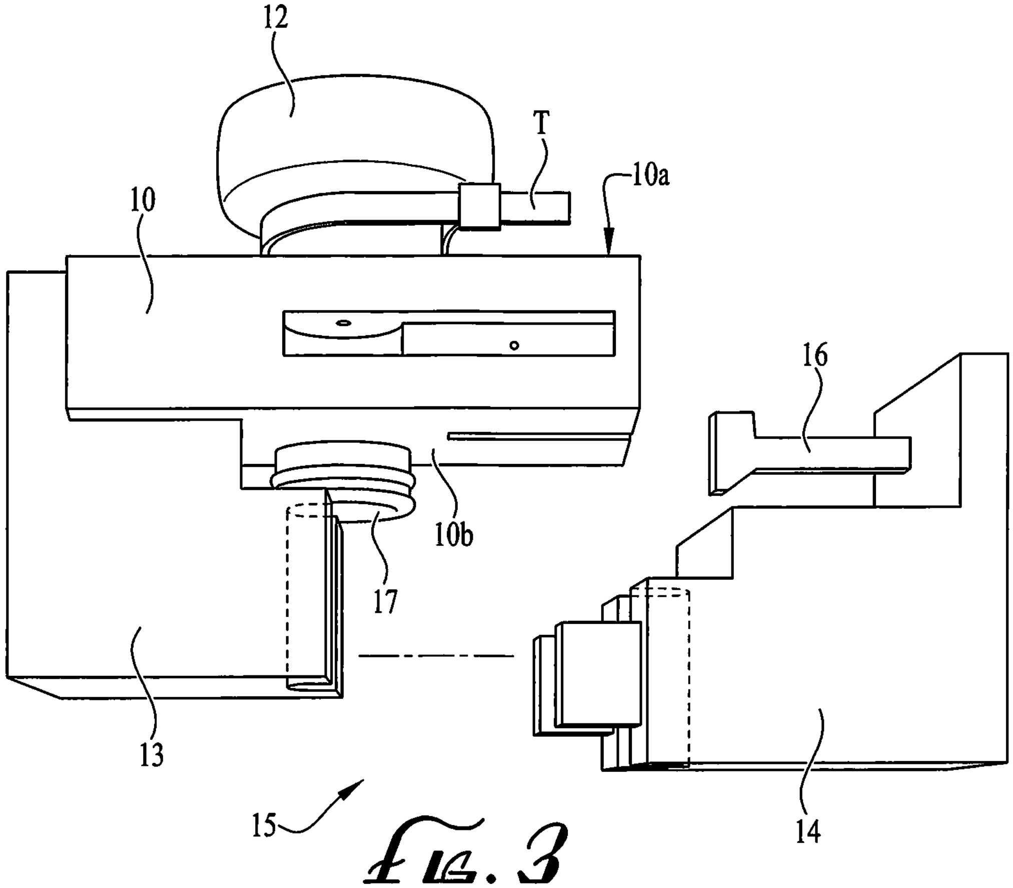
FIG. 3 is a perspective view of a partially uncoupled catheter hub in position next to a longitudinal shearing device according to one embodiment of the present invention.

FIG. 3 is a perspective view of a partially uncoupled catheter hub 10 in position next to a longitudinal shearing blade according to one embodiment of the present invention. In this view, silicone ring 12 rests on the top face 10*a* of catheter hub 10, while the longitudinal shearing device 15 consisting of two parts, 13 and 14, connects to the bottom face 10*b* of catheter hub 10. Also present on the bottom face 10*b* of the catheter hub 10 is female luer lock connector 17, which can be used to secure additional connectors, tubing, drainage bags, or other devices as needed by the patient once the catheter is in place. Catheter hub 10 includes a groove configured to receive notched arm 16 of half 14 of the longitudinal shearing device 15, thereby securing the two pieces of the shearing device 15 together. When the catheter hub 10 is engaged with a catheter, zip tie T tightens the silicone ring 12 around the catheter, providing additional security. The part 14 and part 13 when brought together form a central channel or mandrel in which a catheter is to be severed with a blade (unshown in FIG. 3). The channel or mandrel acts to hold the catheter in a fixed position as it is severed by the blade.

Figure 4A:
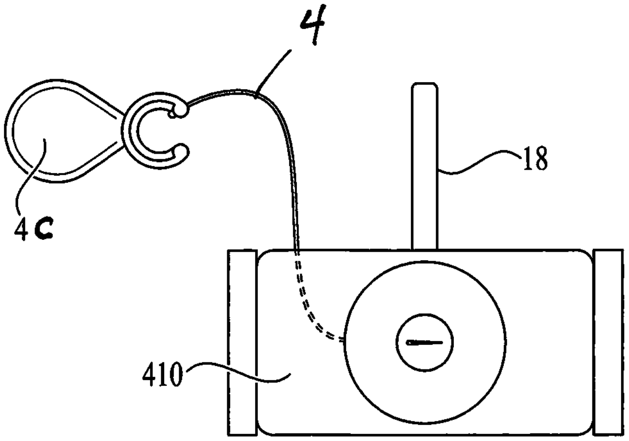
FIGS. 4A-4C are side views of an alternate catheter hub with a locking side arm in relation to a locking stay suture according to another embodiment of the present invention.
Figure 4B:
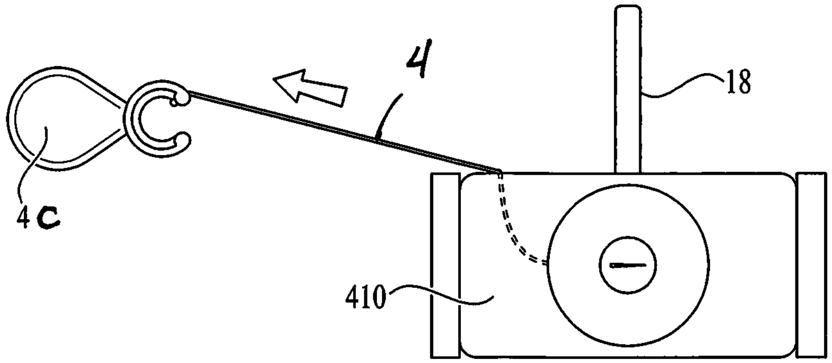
Figure 4C:
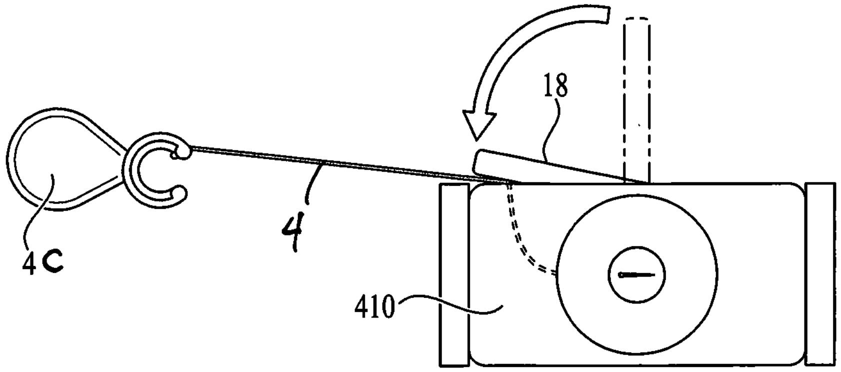

FIGS. 4A-4C are side views of an alternate catheter hub 410 with a locking side arm 18 in relation to the locking stay suture 4 according to another embodiment of the present invention. In FIG. 4A, the locking stay suture 4 has not yet been tightened. In FIG. 4B, the locking stay suture 4 is pulled by handle or clamp 4*c* to achieve tightening. In FIG. 4C, a locking side arm 18 is flipped down over locking stay suture 4 to secure the suture in place. In some alternative embodiments, established methods including ties, clamps, clips, and so forth of securing the locking stay suture 4 in place can be used.

Figure 5:
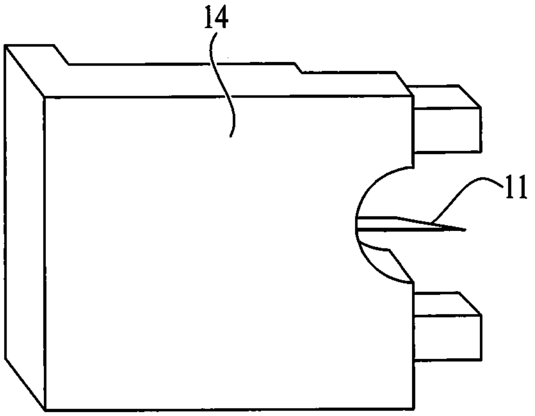
FIG. 5 is a perspective view of a longitudinal shearing blade according to one embodiment of the present invention. The blade extends from one half of a longitudinal shearing device that can be removed from the catheter hub once shearing has been completed.

FIG. 5 is a perspective view of part of the longitudinal shearing device 15 shown in FIG. 3, in particular 14. As shown herein, part 14 includes a longitudinal shearing blade 11 according to one embodiment of the present invention. The blade 11 extends from part 14 toward part 13 (not shown in this figure). Moreover, both halves 13, 14 of the longitudinal shearing device 15 that can be removed from the catheter hub (not shown in this view) once shearing has been completed.

Figure 6:
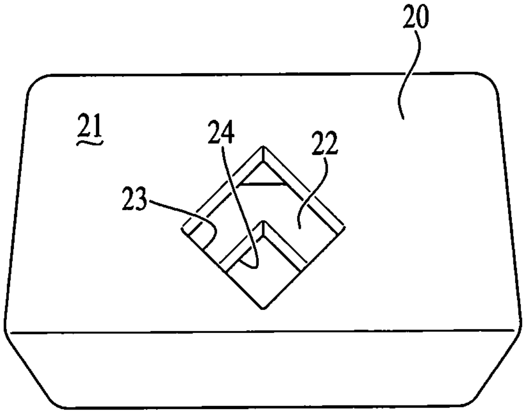
FIG. 6 is a top perspective view of a silicone cover for a catheter hub according to one embodiment of the present invention.

FIG. 6 is a perspective view of a silicone cover 20 for a catheter hub according to one embodiment of the present invention. In alternative embodiments, silicone cover 20 can optionally be tapered or contoured to reduce the profile of the cover and/or for added patient comfort. Silicone cover 20 is made from a soft, non-reactive, medically-safe grade of silicone to avoid rubbing or chafing at the catheter insertion site and may optionally include adhesive to assist in positioning and holding the catheter hub on the patient's body. The cover can have an upper face or panel 21, a lower face or panel 22, and can be provided with apertures 23, 24 therethrough for allowing the catheter and/or catheter hub to extend through the cover 20. While square apertures are depicted, those skilled in the art will appreciate that other shapes of apertures can be used as desired.

Figure 7:
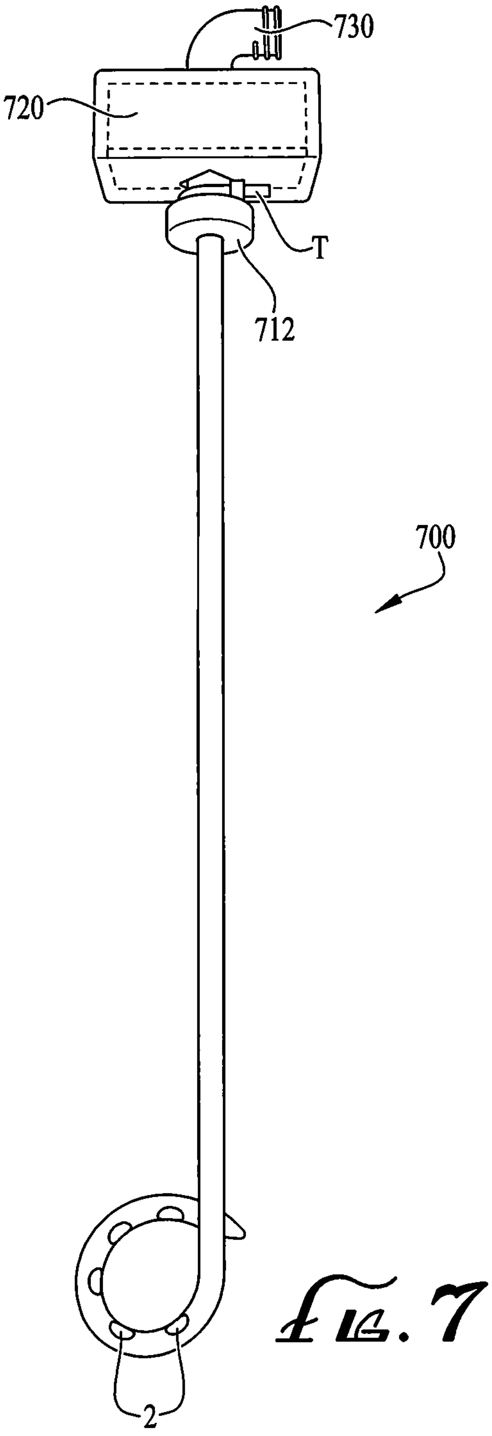
FIG. 7 is a perspective view of an assembled catheter including a catheter hub with silicone cover and an elbowed luer lock connector according to one embodiment of the present invention.

FIG. 7 is a perspective view of an assembled catheter 700 including a catheter hub (not seen in this view) inside silicone cover 720 and attached to an elbowed luer lock connector 730 according to one embodiment of the present invention. In this view, the locking stay suture extending through one of the plurality of side holes 2 has been tightened, as indicated by the pigtail curl in the end of the catheter. Further in this view, zip tie T has been placed around silicone ring 712 to grip and further secure the catheter.

Figure 8A:
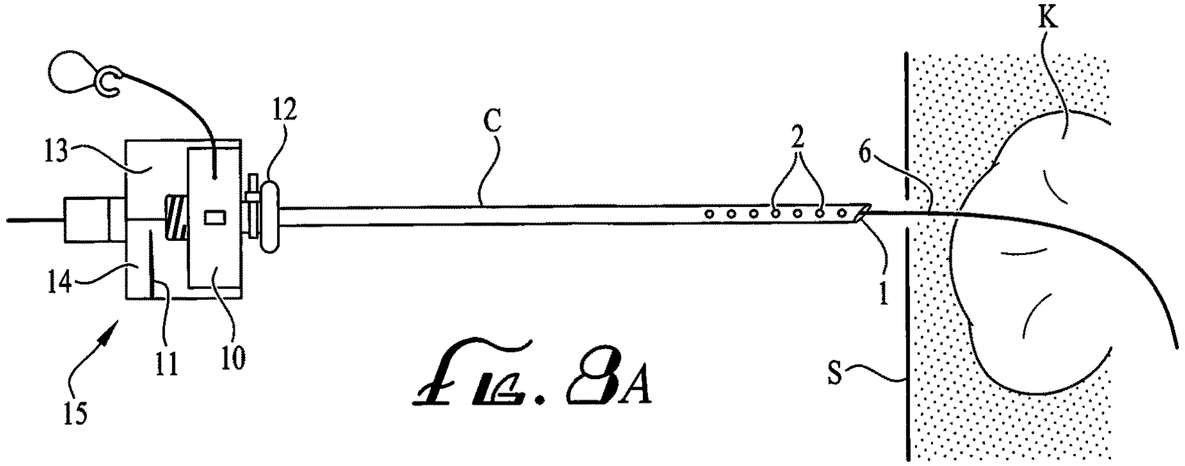
FIGS. 8A-8I are schematic views of example systems and methods according to embodiments of the present invention.

FIGS. 8A-8I are schematic views of example systems and methods according to embodiments of the present invention. In FIG. 8A, a catheter C containing an internal locking stay suture is inserted through body surface S into an organ K or area of interest by placing the end hole 1 over a sharp needle stylet 6 that has been previously directed into the organ by an interventional radiologist. Catheter hub 10 contains a silicone ring 12 and is connected to halves 13 and 14 of the longitudinal shearing device containing longitudinal shearing blade 11. Catheter hub 10 is placed at the proximal end of catheter C, away from the patient's body surface S.

Figure 8B:
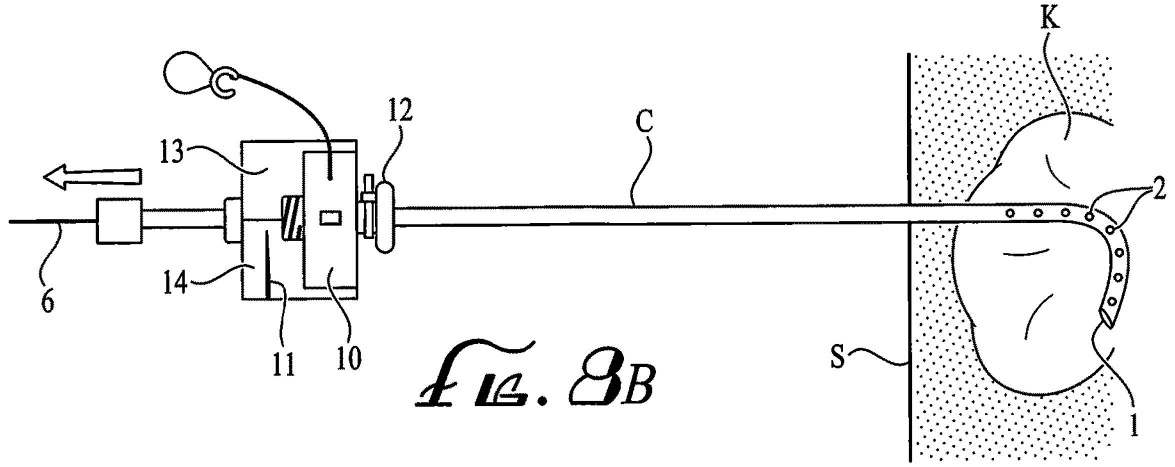
Figure 8C:
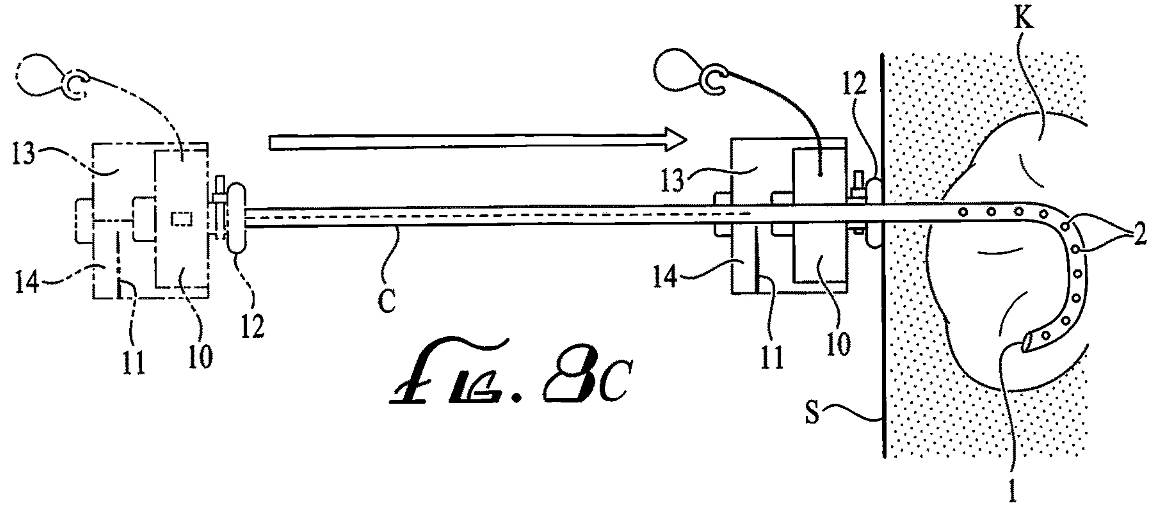
Figure 8D:
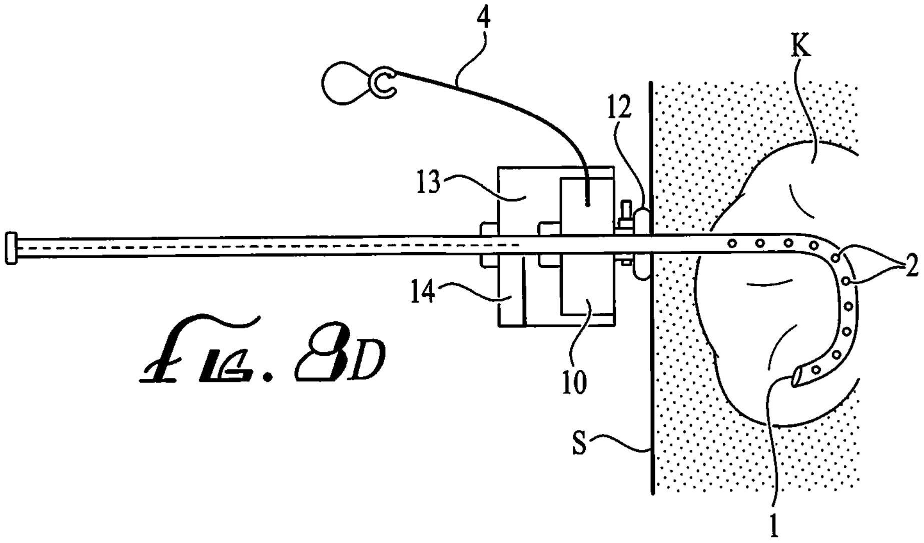
Figure 8E:
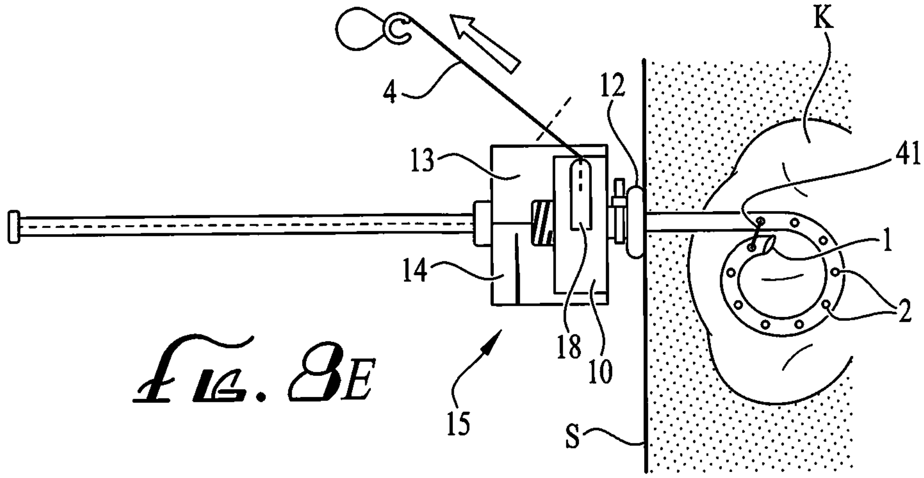

In FIG. 8B, the sharp needle stylet 6 is removed from the catheter C. In FIG. 8C, catheter hub 10 and longitudinal shearing blade 11 are advanced along the catheter C until the silicone ring 12 on the hub 10 is flush with a patient's body surface S, creating a longitudinal cut along the axis of the catheter. In FIG. 8D, the proximal end 41 of the locking stay suture 4 is slipped through a longitudinal cut in the catheter C. In FIG. 8E, the proximal end 41 of locking stay suture 4 is tightened by pulling or another mechanism, forming a pigtail structure or curl in the distal end of the catheter by pulling a end hole 1 towards one of the plurality of side holes 2 using the distal end 41 of locking stay suture 4, securing the catheter in the organ or area of interest K. The suture is then secured by any of several mechanisms such as, for example, by depressing a locking side arm 18 on the catheter hub 10 to hold the suture in place, maintaining the pigtail structure to prevent the catheter from pulling or slipping out of the insertion site.

Figure 8F:
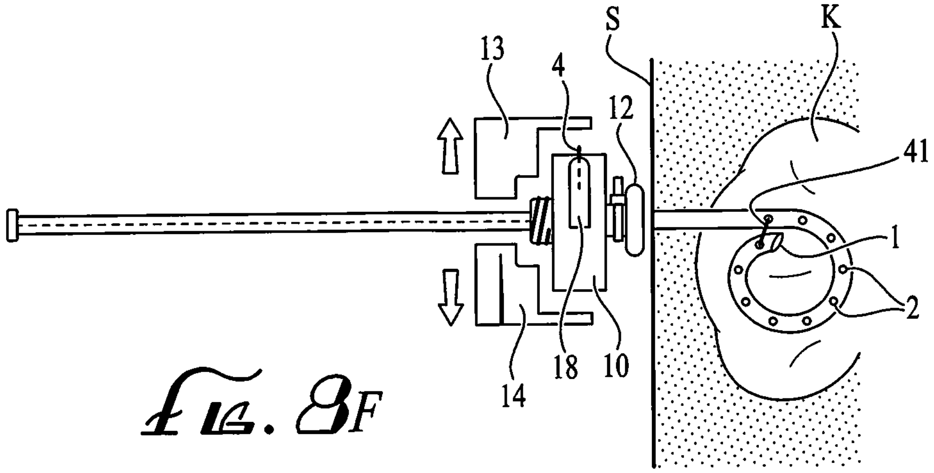
Figure 8G:
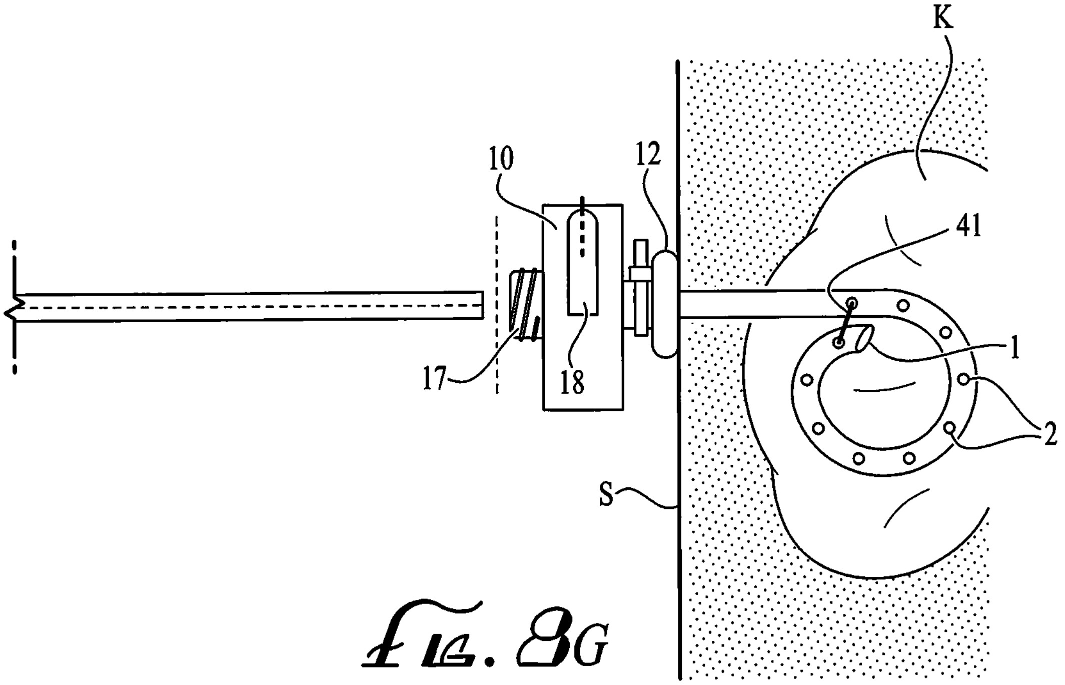

In FIG. 8F, the halves 13 and 14 of the longitudinal shearing device are removed from the catheter hub 10. In FIG. 8G, the catheter can be cut at the base of a female luer lock connector 17 on the catheter hub 10 and the hub can be tightened around the catheter at the silicone ring 12 by any of several means including the use of a zip tie. Since the locking stay suture has already been pulled out of the longitudinally-cut section of the catheter and distal end 41 secured (e.g., by a locking side arm 18 or another method), the pigtail curl structure remains in the distal end of the catheter, keeping the catheter in place, and catheter base/hub 10 is flush against body surface S with no excess tubing protruding.

Figure 8H:
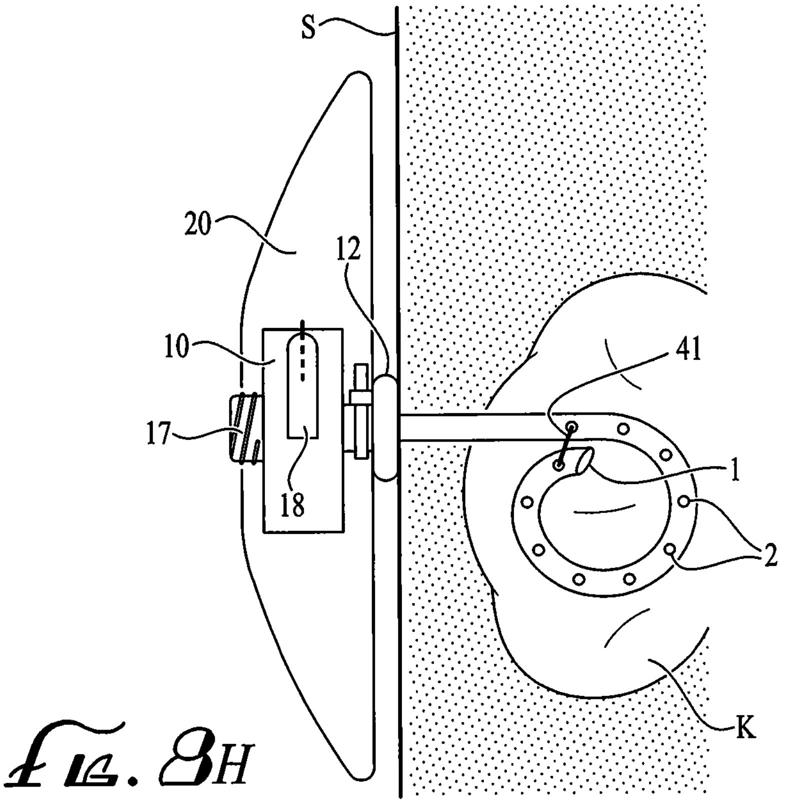
Figure 8I:
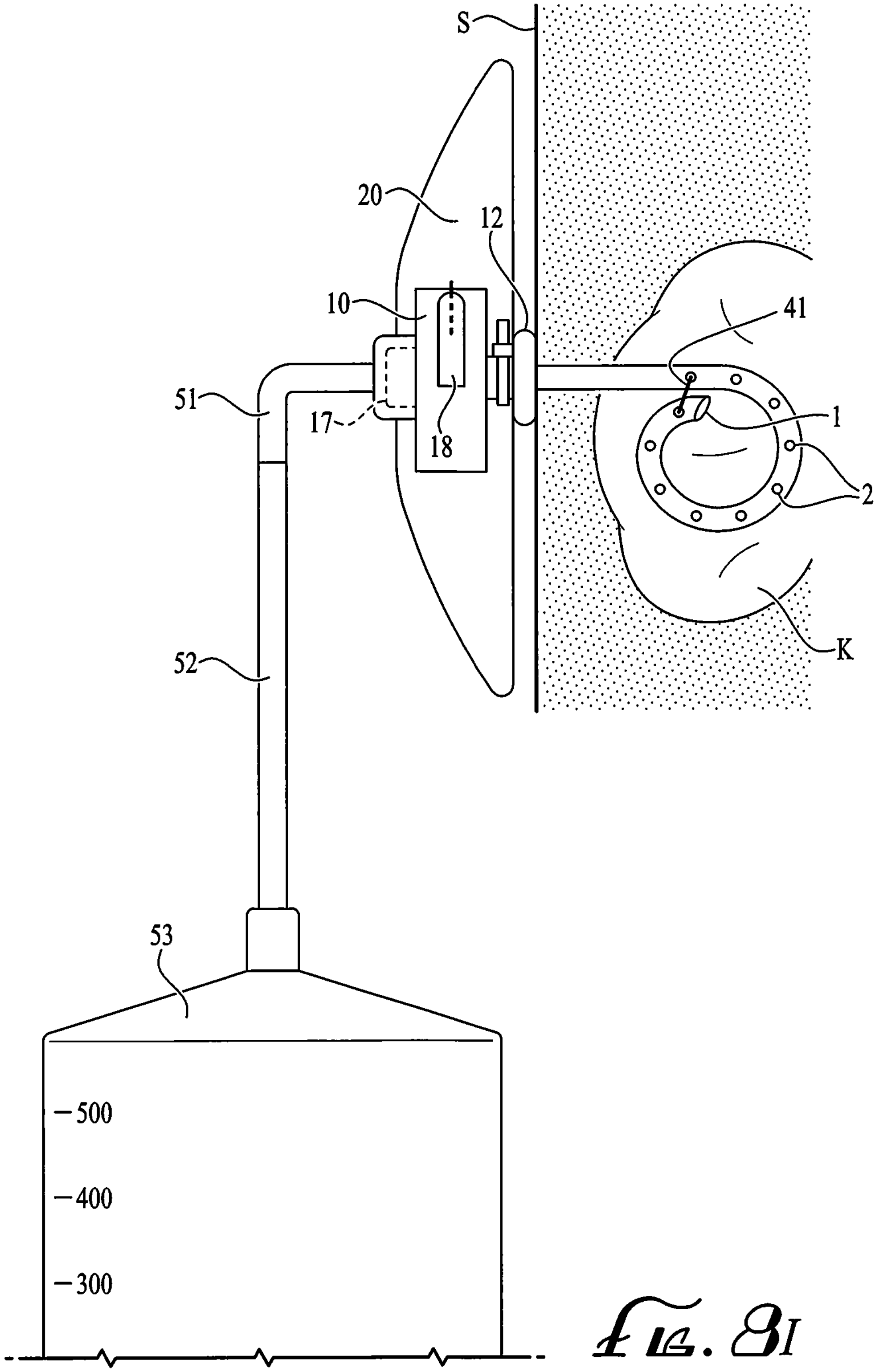

In FIG. 8H, a soft silicone cover 20 can be placed over the hub 10 at the skin S. The cover 20 may be tapered, contoured, or padded to increase patient comfort and prevent the catheter from being pulled out and may have adhesive on one side to adhere the cover to the skin. In FIG. 8I, the female luer lock connector 17 on the catheter hub 10 is used for connecting a standard or elbowed luer lock connection 51 which can then be connected to tubing 52 and a collection bag 53 or another device as needed. In some embodiments, an elbowed luer lock connection 51 allows drainage tubing 52 to follow the body profile, allowing for securing collection bag 53 comfortably under clothing.

Thus, in example embodiments, the present invention provides a universal drainage catheter kit and system and method of adjusting the same to account for different insertion depths, patient body conditions, and the like. In example forms, the catheter kit includes a catheter having an elongate body, a separate hub configured to surround the elongate body of the catheter, and a longitudinal shearing device configured to attach to the hub.

In one aspect, the present invention includes a catheter having an elongate body extending a length along a longitudinal axis from a proximal first end to a distal second end, the second end configured for insertion into an organ or cavity of a patient. The catheter further has an end hole at the distal second end as well as a plurality of distal side holes. When the catheter is placed in a patient, drainage of fluids from a cavity or organ in the patient is accomplished by fluid flow into the end and/or side holes, through the body of the catheter, and out through the hub to tubing, a drainage bag, pump, syringe, or other collection device. In some aspects, the collection device can be removed and the hub can be capped if drainage is not required for the moment but catheter removal is not yet indicated. The elongate body of the catheter is constructed from a sturdy, flexible material that can be sheared with a blade but is not typically torn or damaged under conditions of regular use. The elongate body surrounds a locking stay suture extending from an attachment point at the end hole of the distal second end, through one of the side holes, through the elongate body of the catheter along the longitudinal axis, and out through the proximal first end of the catheter. In one aspect, the flexible material of the hub contributes to increased patient comfort.

In another aspect, the invention relates to a hub and longitudinal shearing device configured to attach to the catheter. In example forms, the hub and longitudinal shearing device are manufactured separately from the catheter and are placed on the catheter at the time of insertion and adjustment. The hub is molded of plastic or a similar stiff material and includes a first surface and a second surface. The first surface of the hub is configured to attach to the longitudinal shearing device and further incorporates a female luer lock connector for attachment to tubing, a cap, or a collection device as described previously. The second surface of the hub includes a silicone ring configured to surround the elongate body of the catheter. A channel extends from the opening of the silicone ring, through the body of the hub, allowing for the hub to advance along the placed catheter towards a body surface of the patient. The hub optionally includes a locking arm that can be flipped down to secure the locking stay suture, or another feature to secure the locking stay suture, for example by winding, tying, clamping, and so forth. The longitudinal shearing device contains a blade capable of producing a longitudinal cut along the longitudinal axis of the catheter without damaging the locking stay suture inside the catheter. In example forms, the longitudinal shearing device includes two portions that can be removed from the hub separately once shearing has been completed.

In still another aspect, the invention relates to a method for inserting a catheter into a patient, securing the catheter in the patient, and adjusting the catheter length so that the catheter hub rests against the patient's body with no parts of the catheter extending past the hub or projecting outwardly from the body surface. In one example system and method, a catheter having an elongate body extending along a longitudinal axis and containing an internal locking stay suture is inserted through a body surface into an organ, cavity, or other area of interest by placing the end hole over a sharp needle stylet that has been previously directed into the area by an interventional radiologist. A metal stiffening cannula may also be used to guide catheter placement; if used, this cannula is removed prior to removal of the sharp needle stylet. The catheter hub attached to the longitudinal shearing device is placed at the proximal end of the catheter, away from the patient's body surface and with the silicone ring facing the body surface.

In example forms, the catheter hub and longitudinal shearing device are advanced along the catheter until the silicone ring on the hub is flush with a patient's body surface, creating a longitudinal cut along the axis of the catheter. The longitudinal shearing device is then removed from the catheter hub. The proximal end of the locking stay suture is then slipped through the longitudinal cut in the catheter and tightened by pulling or another mechanism, forming a pigtail structure or curl in the distal end of the catheter by pulling the end hole toward one of the plurality of side holes, securing the catheter in the organ or area of interest. The suture is then secured by any of several mechanisms such as, for example, by depressing a locking side arm on the catheter hub to hold the suture in place, or by tying, winding, or clamping, thereby maintaining the pigtail structure to prevent the catheter from pulling or slipping out of the insertion site.

Once the locking stay suture is secured, preferably the excess catheter containing the longitudinal slit can be cut using shears or another bladed device. A zip tie or other means can then be used to tighten the silicone ring of the hub around the catheter. In example forms, a soft silicone cover is placed over the hub at the body surface. The cover can be tapered, contoured, or padded to increase patient comfort and prevent the catheter from being pulled out and can have adhesive on one side to adhere the cover to the skin. A luer lock connector on the hub can then be used as an attachment point for tubing, a syringe, a pump, a collection bag, or a cap, as needed.

In one aspect, the drainage catheter is capable of sustaining a drainage flow rate of at least 2.4±0.3 mL/s of fluid with no external applied forces (i.e., no pumping). Thus, at the low end, the drainage catheter is capable of sustaining a drainage flow rate of at least 2.1 mL/s of fluid with no external applied forces. In other instances, the drainage catheter is capable of sustaining a drainage flow rate of at least 2.7 mL/s of fluid with no external applied forces. In example forms, the pigtail curled structure can withstand greater than 2 pounds of pulling force without becoming uncurled and without the catheter becoming dislodged from the body or the placement site within the body.

In other aspects, the system and method described herein contain numerous features designed to enhance patient comfort. The elongate body of the catheter is flexible rather than rigid, which prevents pain or discomfort from motion. The external port (luer lock connector) of the catheter is flush with the base of the catheter, and the base rests against the patient's skin, so no portion of catheter extends away from the body unsupported. Although the base is made from a stiff material, it is surrounded by a silicone cover that can possess optional features (tapering, contouring, and/or padding) to prevent pressure from the hub against the skin. The silicone cover can further be attached to the patient's skin with adhesive to prevent friction or rubbing injuries. If a portable drainage bag is required, it can be secured against the patient's body, under clothing, presenting an unobtrusive profile and allowing for the patient to dress normally.

While the invention has been described with reference to example embodiments, it will be understood by those skilled in the art that a variety of modifications, additions and deletions are within the scope of the invention, as defined by the following claims.

What is claimed is:

1. A drainage catheter system comprising:

a catheter having an elongate body extending a length along a longitudinal axis from a first end to a second end, and having an end hole at the second end and a plurality of side holes between the first end and the second end;

a hub configured for engagement with the catheter and movable along the length of the elongate body of the catheter, a silicone cover for placement over the hub, and having an inner surface configured for adhesive contact with a skin surface of a patient upon placement of the catheter, and a tapered outer surface opposite the inner surface;

a longitudinal shearing device comprising a blade configured to move along the length of the elongate body of the catheter and produce a longitudinal cut through and along the elongate body of the catheter; and a locking stay suture attached to the catheter second end and extending through the length of the elongate body of the catheter;

wherein the longitudinal shearing device does not cut the locking stay suture when it produces the longitudinal cut through and along the elongate body of the catheter.

2. The drainage catheter system of claim 1, wherein a portion of the locking stay suture can be pulled through catheter and tightened to pull the second end of the catheter into a curled configuration.

3. The drainage catheter system of claim 1, wherein the hub further comprises a hinged locking arm configured to flip down over the locking stay suture to prevent the locking stay suture from loosening.

4. The drainage catheter system of claim 1, wherein the elongate body of the catheter comprises a flexible material.

5. The drainage catheter system of claim 1, wherein the hub further comprises a silicone ring configured to rest against the skin surface of the patient upon placement of the catheter, and wherein the silicone ring fully surrounds a portion of the elongate body of the catheter.

6. The drainage catheter system of claim 5, wherein the hub is configured to be further secured to the catheter by tightening a zip tie around the silicone ring.

7. The drainage catheter system of claim 1, wherein the hub further comprises a luer lock adapter.

8. The drainage catheter system of claim 1, further comprising a metal stiffening cannula configured to extend at least partially into the catheter to assist in catheter insertion, and to be removed following catheter insertion leaving the catheter in place.

* * * * *